Figure 1:
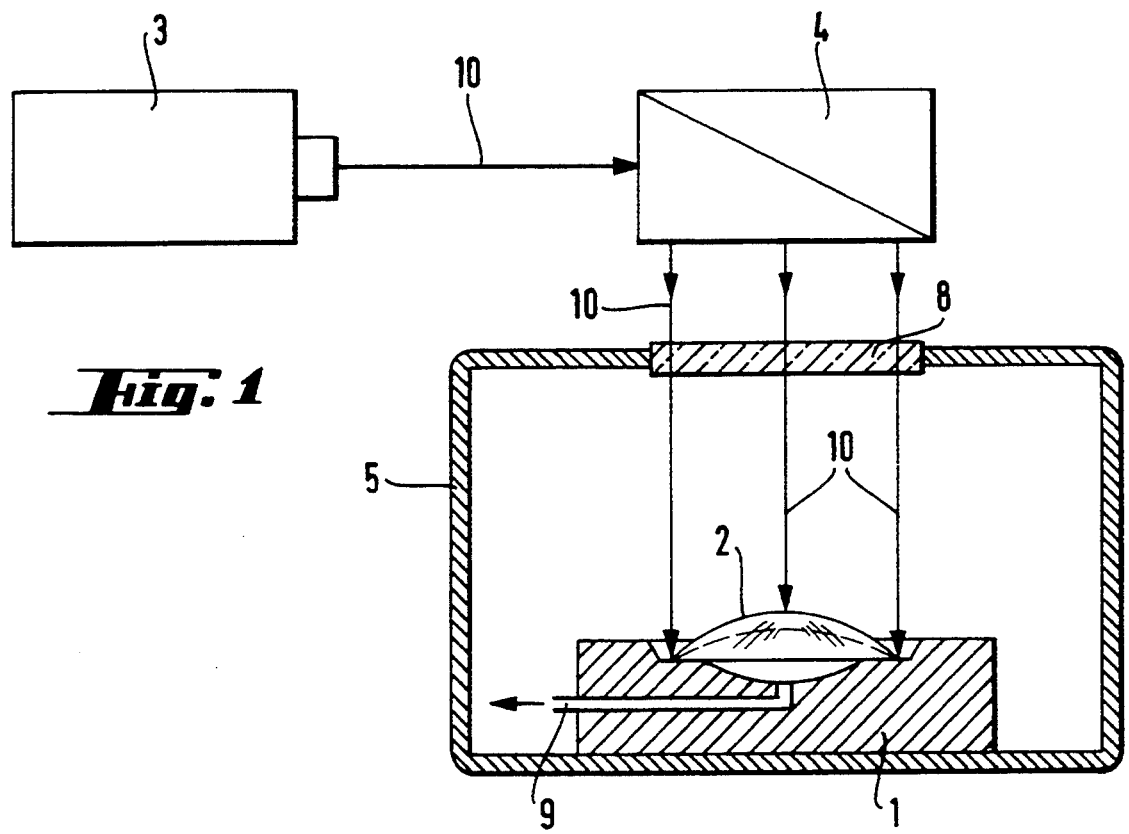

United States Patent

Hagmann et al.

Patent Number: 5,439,642
Date of Patent: Aug. 8, 1995

[54] METHOD OF SURFACE-CLEANING AND/OR STERILIZING OPTICAL COMPONENTS, ESPECIALLY CONTACT LENSES

[75] Inventors: Peter Hagmann, Hösbach-Bahnhof; Peter Höfer, Aschaffenburg; Peter Herbrechtsmeier, Königstein, all of Germany

[73] Assignee: Ciba-Geigy Corporation, Ardsley, N.Y.

[21] Appl. No.: 220,943

[22] Filed: Mar. 31, 1994

Related U.S. Application Data

[63] Continuation of Ser. No. 5,922, Jan. 19, 1993, abandoned, which is a continuation of Ser. No. 765,604, Sep. 25, 1991, abandoned.

[30] Foreign Application Priority Data

Oct. 2, 1990 [CH] Switzerland .......... 3208/90

[51] Int. Cl.$^6$ .......... A61L 2/08; A61L 2/10
[52] U.S. Cl. .......... 422/22; 422/24; 250/455.11; 351/160 R
[58] Field of Search .......... 422/22, 24; 134/901; 351/160 R, 177; 250/455.11

[56] References Cited

U.S. PATENT DOCUMENTS

| | | |
|---|---|---|
| 3,833,786 | 9/1974 | Brucker .......... 351/177 |
| 3,852,032 | 12/1974 | Urbach .......... 21/54 R |
| 4,115,280 | 9/1978 | Pratt, Jr. .......... 250/527 |
| 4,194,814 | 3/1980 | Fischer et al. .......... 351/160 R |
| 4,209,252 | 6/1980 | Arditty et al. .......... 356/4 |
| 4,263,054 | 4/1981 | Giambaluo .......... 134/21 |
| 4,307,046 | 12/1981 | Neefe .......... 264/1.4 |
| 4,563,565 | 1/1986 | Kampfer et al. .......... 219/121 LJ |
| 4,868,397 | 9/1989 | Tittel .......... 422/24 X |
| 4,899,057 | 2/1990 | Koji .......... 422/24 X |
| 5,061,342 | 10/1991 | Jones .......... 156/643 |
| 5,068,514 | 11/1991 | Lunney .......... 219/121.69 |
| 5,098,618 | 3/1992 | Zelez .......... 264/22 |

FOREIGN PATENT DOCUMENTS

| | | | |
|---|---|---|---|
| 3722384 | 1/1989 | Germany .......... | 422/24 |
| 9110455 | 7/1991 | WIPO .......... | 422/24 |

*Primary Examiner*—Robert J. Warden
*Assistant Examiner*—E. Leigh Dawson
*Attorney, Agent, or Firm*—Edward McC. Roberts; R. Scott Meece

[57] ABSTRACT

In order to remove impurities and contaminations adhering to the surfaces of an optical component, especially to the front and rear faces of a contact lens, electromagnetic radiation is caused to act on the optical component. Using that electromagnetic radiation, preferably the light of an excimer laser the wavelength, energy density and intensity of which are adjustable, the adherent impurities and any microorganisms present are killed, deactivated and removed photo-ablatively.

13 Claims, 1 Drawing Sheet

METHOD OF SURFACE-CLEANING AND/OR STERILIZING OPTICAL COMPONENTS, ESPECIALLY CONTACT LENSES

This application is a continuation of application Ser. No. 08/005,922, filed Jan. 19, 1993, abandoned, which is a continuation of Ser. No. 07/765,604 filed Sep. 25, 1991, abandoned.

The invention relates to a method of surface-cleaning and/or sterilising optical components, especially contact lenses.

The manufacture of optical components, for example lenses, prisms or optical flats, is carried out in a large number of individual production steps. Practically every production step and the necessary accompanying manipulation and handling of the optical components contribute to the soiling of the surfaces of the components. For example, lenses are secured to corresponding supports in the individual turning, milling, grinding and polishing steps. The lenses are, for example, bonded to the supports by means of wax. When the treatment is complete, the lenses are removed from the supports again and are carefully cleaned of the wax residues. It is preferable to use cleaning fluids to clean the lenses. The impurities are removed from the lens surfaces in a large number of individual cleaning steps, which include, inter alia, immersion of the lens in the cleaning fluid, abrasion, ultrasound treatment, rinsing and finally drying of the lens.

In spite of the effort that goes into cleaning the lenses, the result is often unsatisfactory since it is not possible to remove all the residues from the lens surfaces completely and they remain attached to the surfaces or at least to parts thereof in the form of a thin film. These residues can then, however, lead to an impairment of the functional properties of the optical components. In addition, the cleaning fluids often contain substances that are detrimental to the environment. When they are handled, they can give rise to undesirable allergies in the operating personnel despite extensive precautions, for example removal by suction and protection against direct contact.

In the case of contact lenses, these residues resulting from the production process are often thin wax films having a layer thickness of, as a rule, less than 1 μm. The residues may also be the remains of polishing and cleaning agents, or often residues of grease from fingerprints. Such residues can lead in contact lenses to considerable wetting problems and thus to a reduction in the tolerability of the contact lenses. The residues can, however, also act as adhesion centres for deposits on the contact lenses and must therefore be removed. In many cases the contact lenses are also sterilised, before being packed in a germ-free solution without preservatives, in order to exclude harmful side-effects caused by germs on the surfaces of the lenses when the contact lenses are in use. Such sterilisation has hitherto been carded out, for example, in accordance with processes using hot air or damp heat, and microbicidal gases are often also used. Those processes can, however, be used only when the sterilisation conditions do not result in damage to the contact lens, or, quite generally, do not result during sterilisation in damage to the material from which the optical components are produced. Treatment with hot air or damp heat at temperatures above 160° C. is not suitable, for example, for many contact lens materials since the lens material can be damaged thereby or geometrical deformation may occur. When gas sterilisation is used, normally with ethylene oxide, undesired storage of the gas in the lens material frequently occurs, and, especially in the case of intraocular lenses, residues of the sterilisation gas can give rise to complications which may often lead even to the explantation of the lens.

U.S. Pat. No. 4,223,782 describes a conventional device for the cleaning and subsequent rinsing of contact lenses by means of a cleaning fluid and a rinsing fluid, such as are used, for example, by contact lens wearers for daily lens treatment. That device is not, however, suitable for removing impurities resulting from the production process that adhere to the surface of a contact lens.

U.S. Pat. No. 3,852,032 describes a method of sterilising soft contact lenses using ultraviolet radiation. The method described can, however, be used only with contact lenses the lens materials of which contain UV stabilisers that, for example, absorb some of the energy of the ultraviolet radiation in order to prevent the lens material from being damaged.

FR-A-2 539 030 describes a further method of sterilising contact lenses using ultraviolet radiation and a suitable device therefor. In order to prevent damage to the lens material by UV radiation having a wavelength of 273.7 nm, the energy density of the UV radiation is maintained at a relatively low level, typically approximately 0.04 J/cm$^2$. That treatment is, however, not suitable for a reliable removal of impurities from the surface of a contact lens.

U.S. Pat. No. 4,115,280 describes a device for changing the biological and chemical activity of macromolecules. The device comprises a source for infrared radiation by means of which an object to be treated is irradiated. The device is not suitable for removing impurities from the surface of an optical component, for example a contact lens.

The problem is accordingly to provide a method of cleaning and sterilising surfaces of optical components, especially the front and rear faces of contact lenses, which method eliminates the mentioned disadvantages. The method is to be easy and economical to carry out and is to be suitable for easy automation of the procedure. In addition, cleaning agents and sterilising gases that are detrimental to the environment are to be avoided. There is, however, a special desire to provide a method in which the surface-cleaning and/or sterilisation of the optical components, especially the contact lenses, is carried out in one operation. The surfaces of the optical components are to be substantially free of residues when the treatment is complete, and microorganisms present on the surfaces are to be killed, deactivated or removed.

Those and other problems are solved by a method according to the present invention.

Figure 2:
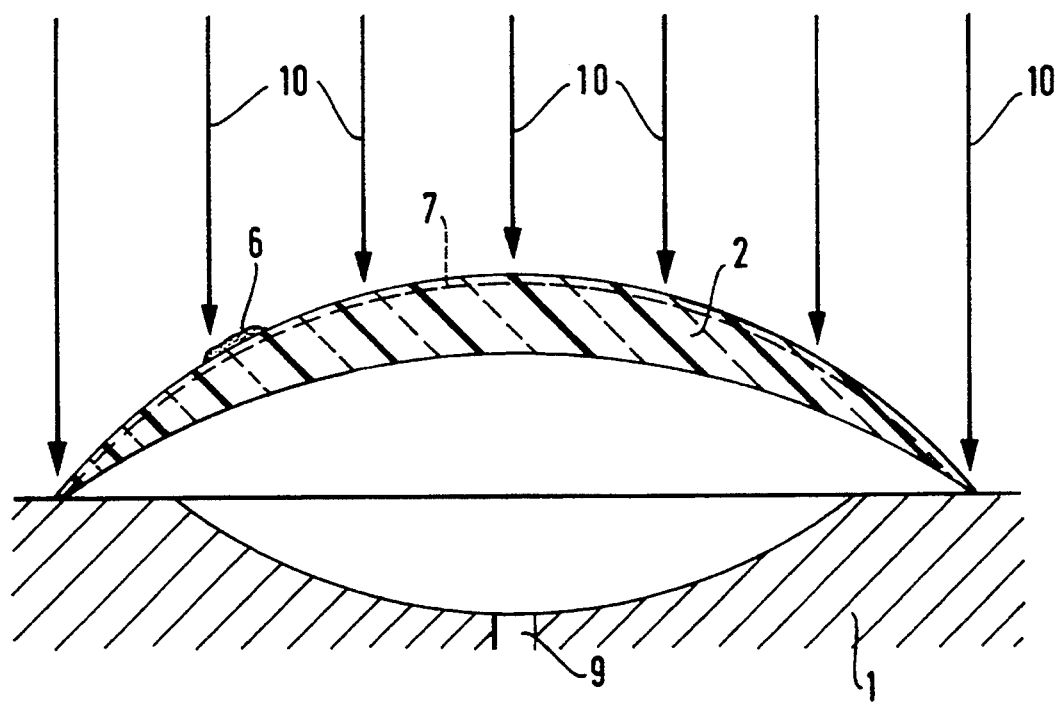

The method according to the invention is explained in more detail hereinafter with reference to the drawing, in which FIG. 1 shows a schematic diagram of a device for carrying out the method according to the invention and FIG. 2 shows a contact lens with impurities, and the shape of the front face, indicated by a broken line, after the treatment according to the invention.

FIG. 1 shows a schematic diagram of an example of a device for carrying out the method according to the invention. The device is especially one for treating contact lenses. It goes without saying that the device shown schematically may, if desired, be modified for the treatment of optical lenses, prism faces or spectacle lenses etc.. According to the diagram, the device essentially comprises a support 1 for an optical component 2 to be treated, in this case a contact lens, and a radiation source 3 for electromagnetic radiation 10 together with an optical arrangement 4. The radiation source 3 for the electromagnetic radiation 10 is a laser, preferably a so-called excimer laser (excimer from excited dimer). The optical arrangement 4, depending on the purpose for which it is used, comprises focusing means and/or beam-spreading means and, where appropriate, beam-deflecting means. The support 1 may, for example, be in the form of a circulating belt. The lenses 2 are introduced into the supports 1 at a loading station (not shown) and fixed in position, for example, by means of a slight partial vacuum. This is symbolised in FIG. 1 by a partial vacuum line 9. The support 1 is preferably arranged inside a housing 5. The housing 5 has one or more windows 8 that are transparent to the electromagnetic radiation used but it may also be constructed to be entirely transparent. The lenses 2 are introduced into the housing by way of an insertion and removal lock. After treating one lens face, the lens is turned round in the loading station and introduced into the housing 5 again by way of the lock. The support 1 for the contact lens may, however, also be rotatable about its longitudinal axis by at least 180°. In that manner, the contact lens 2 can be turned in relation to the laser beam so that the laser beam acts on the front and the rear face of the lens. The housing 5 also has air-extraction and disinfection means (not shown). In that form, the inside of the housing can be maintained in a substantially germ-free state so that the treatment of the contact lens can be effected in a sterile environment. It is of course possible for the entire device itself to be arranged in a sterile chamber, in which case the housing 5 would be superfluous. The contact lens 2 may also still be contained, for example, in one half of a casting mould, and the support 1 may be in a form suitable for receiving the mould half.

In order to clean and/or sterilise the front and rear faces of the contact lens 2, the latter is arranged in the preferably automatically rotatable support 1 in the path of the beam of the excimer laser 3. The surface-cleaning and sterilisation of the contact lenses 2 are carded out by causing laser radiation 10 of a specific wavelength, energy density and intensity to act on the surfaces of the contact lenses 2. The impurities adhering to the front and rear faces of the contact lens 2 are thereby removed ablatively and, in the same operation or in a separate sterilisation step, any microorganisms present are killed, deactivated or likewise removed photo-ablatively.

The laser beam 10 preferably acts on the entire front and rear faces of the contact lens 2 and for that purpose the laser beam coming from the excimer laser 3 is spread by means of the beam-spreading means. By a suitable choice of wavelength for the laser light, which wavelength, in the case of the excimer laser, can be adjusted easily, for example by exchanging or altering the amplifying medium, and by a suitable choice of energy density and intensity therefor, the impurities and/or contaminations can be removed selectively from the lens surface without damaging the surface of the contact lens 2.

In an alternative method, the surfaces of the contact lens 2 are scanned by a low-energy laser beam before surface-cleaning and/or separate sterilisation, and the impurities and contaminations are detected in laser-interferometric manner and their spatial distribution on the contact lens 2 is recorded. The scanning of the lens surfaces can be carded out, for example, in a separate surface-inspection station using an additional auxiliary laser, but it is also possible to use the excimer laser 3. For the purpose of scanning, the excimer laser 3 is operated in a low-energy mode. The detected and stored coordinates of the impurities are fed to focusing and beam-deflecting means with the aid of which the working laser can then be directed onto the detected impurities and contaminations in order to remove them.

Instead of scanning the focused laser beam 10 over the lens surface, the lens surface can be irradiated as a whole, the uncontaminated areas of the lens surface being covered by a mask, for example an LCD mask, that can be influenced area by area in respect of its transmission. The wavelength, the energy and the intensity of the laser beam 10 are again such that the impurities and/or any contamination present are removed selectively without damaging the surface of the contact lens 2.

The wax residues often adhering to the contact lenses are generally very thin, usually less than 1 μm thick. In a variant of the method, in the case of full-face irradiation of the front or rear face of the contact lens, the method parameters, such as wavelength of the laser light, energy density and intensity of the laser beam, are so chosen that the impurities and/or any contamination present are removed together with a thin surface layer of the lens 2. The method parameters are especially so chosen that a surface layer of no more than 1 μm thick is removed in the areas having no impurities. Although the temporary masking effect of the impurities results in a slight structuring of the lens surface, the depth of the steps is no more than 1 μm and does not have a detrimental effect on the manner in which the contact lens 2 functions. FIG. 2 shows a section through a contact lens 2 having impurities 6. The broken line 7 indicates the shape of the front face of the contact lens 2 after laser treatment.

This variant of the method of full-face material removal from contact lens surfaces is also especially suitable in the case of lenses 2 that have thin surface layers having material properties differing from those of the basic material of the lenses. Such lenses may occur in the case of the so-called "full mould" method in which the contact lens 2 is produced in a one-stage method by polymerising a liquid polymerisation batch in a casting mould. The surface layers that sometimes occur during polymerisation owing to surface effects and interfacial effects between the lens material and the casting mould can be removed over the entire face. The lens material of deeper layers, which material exhibits the desired bulk material properties unaltered, is exposed without any substantial effect on the basic geometry of the contact lens 2.

In order to carry out the surface-cleaning and sterilisation method according to the invention, the wavelength of the laser radiation is adjusted to from approximately 100 nm to approximately 350 nm. It goes without saying that laser radiation of the given wavelength ranges can also be achieved with lasers other than excimer lasers. It is also possible to use a laser providing longer wavelengths. In the case of such a laser, the desired wavelength ranges are obtained, for example, by frequency doubling. The energy densities are selected to be from approximately 0.1 $J/cm^2$ to approximately 10 $J/cm^2$. For even better control of the energy deposition of the laser, the latter is driven preferably in pulsed-mode operation.

In all, the method according to the invention enables the surfaces of optical components to be cleaned, and, if desired, to be sterilised in the same or in a separate operation, in a simple, time-saving and inexpensive manner. Especially contact lenses made of hard, highly oxygen-permeable materials, which are very temperature-sensitive, can be readily sterilised in that manner. The irradiation can be carried out in a sterile environment so that renewed contamination of the lenses can be excluded. The packing of the lenses, especially intraocular lenses, can be carried out immediately afterwards in the same sterile environment, ensuring that the lenses are free of germs. Cleaning fluids and sterilising gases are avoided in the method according to the invention. The lens material is treated in a careful manner and surface damage and lens deformation are avoided. In addition, the method can be readily automated and integrated into existing production methods.

What is claimed is:

1. A method of treating the surface of an optical component having a defined geometry and desirable bulk material properties, comprising the steps of:
    (a) generating radiation by means of a laser, said radiation having a preselected wavelength and a preselected energy density;
    (b) applying said radiation to the surface of an optical component for a period of time sufficient to simultaneously photoablatively remove impurities adhering to said surface of said optical component and sterilize said surface;
    wherein said wavelength, energy density, and period of time of application of said radiation are selected such that said radiation does not substantially alter either the desirable bulk material properties of said optical article or the geometry of said optical component.

2. A method according to claim 1, further comprising the steps of detecting impurities on said surface of said optical component and selectively removing said impurities.

3. A method according to claim 2, further comprising concentrating said radiation on said impurities by means of a mask.

4. A method according to claim 2, further comprising the steps of detecting contaminants on said optical component and selectively removing said contaminants.

5. A method according to claim 1, further comprising applying said radiation to substantially the entire face of each surface of said optical component.

6. A method according to claim 5, further comprising removing said impurities together with a surface layer of said optical component.

7. A method according to claim 6, wherein said surface layer has a thickness no more than one micrometer ($\mu$m).

8. A method according to claim 5, wherein said application of radiation occurs in a sterile environment.

9. A method according to claim 8, further comprising arranging said optical component inside a transparent housing, and subsequent to irradiating a first surface, rearranging said optical component automatically in order to irradiate a second surface.

10. A method according to claim 1, wherein said radiation has a wavelength of about 100 nm to about 350 nm and an energy density of about 0.1 J/cm$^2$ to about 10 J/cm$^2$.

11. A method according to claim 1, further comprising pulsing said laser radiation.

12. A method according to claim 1, wherein said laser is an excimer laser.

13. A method according to claim 1, wherein said optical component is a contact lens.

* * * * *